United States Patent [19]

Quakenbush

[11] Patent Number: 5,245,092
[45] Date of Patent: Sep. 14, 1993

[54] PROCESS FOR PREPARING DINITROTOLUENE WITH LOW BY-PRODUCT CONTENT

[75] Inventor: Allen B. Quakenbush, Lake Charles, La.

[73] Assignee: Olin Corporation, Cheshire, Conn.

[21] Appl. No.: 944,639

[22] Filed: Sep. 14, 1992

Related U.S. Application Data

[63] Continuation-in-part of Ser. No. 824,761, Jan. 17, 1992, abandoned, which is a continuation of Ser. No. 670,131, Mar. 15, 1991, abandoned.

[51] Int. Cl.$^5$ ............................................ C07C 205/06
[52] U.S. Cl. .................................. 568/934; 568/939; 568/940
[58] Field of Search ..................... 568/934, 939, 940

[56] References Cited

U.S. PATENT DOCUMENTS

| | | | |
|---|---|---|---|
| 2,362,743 | 2/1943 | Crater | 568/939 |
| 3,928,395 | 12/1975 | Seha et al. | 568/939 |
| 3,957,889 | 5/1976 | Milligan et al. | 568/939 |
| 4,064,147 | 12/1977 | Thelen et al. | 568/939 X |
| 4,804,792 | 2/1989 | Mason et al. | 568/939 |
| 4,918,250 | 4/1990 | Mason et al. | 568/934 |
| 5,001,272 | 3/1991 | Mason | 568/934 |
| 5,099,078 | 3/1992 | Quakenbush | 568/934 |
| 5,099,080 | 3/1992 | Quakenbush | 568/934 |

Primary Examiner—Robert L. Stoll
Assistant Examiner—John M. Covert
Attorney, Agent, or Firm—F. A. Iskander

[57] ABSTRACT

Process for preparing dinitrotoluene by reacting toluene with concentrated nitric acid. The process reacts toluene with a large excess of concentrated nitric acid at selected conditions to produce a product which has substantially reduced by-product content.

17 Claims, No Drawings

PROCESS FOR PREPARING DINITROTOLUENE WITH LOW BY-PRODUCT CONTENT

CROSS-REFERENCE TO RELATED APPLICATION

This application is a Continuation-In-Part of U.S. application Ser. No. 07/824,761 filed Jan. 17, 1992 and now abandoned, which was a continuation of U.S. application Ser. No. 07/670,131 filed Mar. 15, 1991 and now abandoned.

BACKGROUND OF THE INVENTION

1. Field of the Invention

This invention relates to an improved process for preparing dinitrotoluene by reacting nitric acid with toluene. More particularly, the invention relates to a liquid-phase reaction of toluene with a large excess of concentrated nitric acid at selected conditions to minimize explosion hazards and produce a product which has a substantially reduced by-product content. Dinitrotoluene synthesis with low by-product content avoids operations for product purification and the effluent water treatment problems associated with those operations.

2. Background Of The Invention

Commercial processes for preparing dinitrotoluene (DNT) react toluene with a mixed acid containing nitric and sulfuric acid. Mononitrotoluene (MNT) is produced first, followed by DNT formation. A variety of process schemes are used to increase conventional process efficiency. These schemes synthesize the product in a heterogeneous system comprising an organic liquid phase and an acid liquid phase. Nitration occurs in both phases and is Predominate at the phase interface. The reaction rate is controlled by mass transfer in the system.

During MNT synthesis, a small amount of toluene is oxidized instead of nitrated. An article in Albright & Hanson, Industrial and Laboratory Nitrations, ACS Symposium Series 22, Chapter 8, Hanson et al., Side Reactions During Nitration, pages 133 to 155, describes the oxidation by-products to be mostly cresol and phenol type compounds. Some of the compounds, such as dinitro-ortho-cresol, are highly toxic. These by-products are removed from the DNT by washing with alkaline water, which must then be treated to remove the toxic compounds before it is discharged into public waters. The problems caused by the by-products are further described by C. Hanson et al., supra, on page 133, as follows:

> "By-Product formation represents loss of reactants or nitro product. It is also likely to result in increased costs for the separation and purification of the main product, such as increased capital costs for distillation and washing stages, together with higher operating costs for steam and treatment chemicals."

Additionally, the use of mixed acid systems usually involve reconcentration of the spent sulfuric acid after the nitration reaction. This reconcentration step is time consuming, energy intensive and requires the use of expensive materials of construction.

In view of these disadvantages associated with mixed nitric/sulfuric acid systems, there have been several developments in the prior art to perform gas phase or liquid phase nitrations with concentrated nitric acid in the absence of sulfuric acid. U.S. Pat. No. 2,362,743 discloses a two-step process for the manufacture of dinitrotoluene in the absence of sulfuric acid which comprises (a) nitrating toluene to mononitrotoluene using a nitric acid having a concentration from about 60% to about 75% and a mole ratio of toluene to nitric acid of about 1 to about 3.5 and (b) further nitrating the mononitrotoluene to dinitrotoluene using nitric acid having a concentration of from about 90% to about 100%, and a mole ratio of mononitrotoluene to nitric acid of about 1 to about 3. Although the process of this patent is advantageously conducted in the absence of sulfuric acid, it was found that in step (b), a very high percentage of the nitrated product (up to 25%) based upon the amount of toluene reactant employed does not phase separate from the nitric acid medium. The patent teaches vacuum distillation of the product mixture to isolate the desired dinitrotoluene, which is an expensive and highly energy intensive process step.

U.S. Pat. No. 3,928,395 describes a process for nitrating unsubstituted or substituted benzene at a reaction temperature of $-40°$ C. to $80°$ C. using 90% to 100% nitric acid in the optional and preferred presence of a dipolar aprotic solvent, wherein the reaction is halted by means of a dipolar aprotic solvent.

U.S. Pat. No. 3,957,889 describes an improved process for nitrating toluene or ortho-xylene with nitric acid, the improvement being enhancing the rate of the nitration reaction by carrying it out in the presence of at least an effective amount of anhydrous calcium sulfate or soluble anhydrite.

U.S Pat. No. 4,064,147 describes the preparation of aromatic mononitro compounds (such as mononitrobenzene) by a liquid phase reaction with nitric acid having an acid concentration of between 70 and 100% by weight using a reaction temperature of between $0°$ C. and $80°$ C. When employing a relatively reactive compound such as benzene or toluene as a starting material, this patent teaches that a nitric acid concentration of between 70 and 90% by weight is preferred. The process of the patent requires a ratio of nitric acid plus water to organic components of not below 3 when using 70% nitric acid, and not below 8 when using 100% nitric acid. However, it has been found that such a high acid ratio using 100% nitric acid tends to favor dinitrocompound production, not desired by the process of the patent.

U.S. Pat. No. 4,804,792 describes the nitration of benzene and toluene by contacting these with concentrated nitric acid in the presence of a molten nitrate salt. The patent states that the molten salt serves as a temperature regulator for the reaction and as an isothermal medium for the reactants. A preferred method of contacting the reactants in the presence of the molten salt is stated to be by bubbling the reactants into a bath of the molten salt by means of a carrier gas such as nitrogen. The vapor phase reaction is stated to be carried out at a temperature of between $150°$ and $250°$ C.

U.S. Pat. No. 4,918,250 describes a process for nitrating toluene to DNT and phase separation of the product using an inorganic salt as a phase separation agent. In this patent, DNT is produced in a two-step liquid phase nitration reaction between nitric acid and toluene in the absence of sulfuric acid and solvent. In the process of the patent, an inorganic salt is incorporated into the mixture of DNT and unreacted nitric acid in an amount sufficient to cause phase separation of the mixture in order to facilitate isolation of the DNT from the unreacted nitric acid in the product mixture.

More recent developments and improvements in this field are disclosed in U.S. Pat. Nos. 5,001,272, 5,099,078, and 5,099,080. All these patents relate to the production of DNT by nitration of toluene with concentrated nitric acid using a molar excess of nitric acid. Thus the '272 and '078 patents call for a molar ratio, nitric acid to toluene, of up to about 9:1; whereas, a ratio ranging broadly from about 7:1 to about 20:1 is disclosed in the '080 patent.

DESCRIPTION OF THE INVENTION

This invention has two primary objectives in connection with the production of DNT by the reaction of toluene with nitric acid in the absence of sulfuric acid. The first is to minimize the hazards of explosion associated with such a reaction. The second objective is to produce DNT having a substantially reduced content of phenolic by-product, e.g., preferably less than 350 ppm of cresol. The attainment of these two combined objectives is critical to the successful commercialization of the nitric acid process (as distinguished from the mixed nitric/sulfuric acid process) for making DNT.

In accordance with the invention, it has been found that the foregoing objectives can be achieved under specified reaction conditions by employing a molar ratio of nitric acid to toluene in excess of 14:1 and such acid concentration as to provide an effective product acid concentration of at least 89%. As used throughout the specification and claims herein, the term "effective product acid concentration" means the weight concentration of unreacted acid in the reaction product mixture (i.e., reactor effluent). When a large excess of nitric acid is reacted with toluene to form dinitrotoluene, the resulting reaction product will be made up essentially of dinitrotoluene, water and unreacted or excess nitric acid. The water content will be made up of acid water going into the reaction and water formed as a by-product of the reaction. The effective product acid concentration is calculated as a percentage of the aggregate of the total water and nitric acid in the reaction product mixture or reactor effluent. In actual reaction, such relative proportions of reactants are used to achieve an effective product acid concentration of about 90% to about 96% and most Preferably about 91-94%.

It will become readily apparent that the effective product acid concentration depends on a combination of the concentration of the acid used as a reactant and the molar ratio of acid to toluene. Thus at an acid concentration of say 92%, an effective product acid concentration of at least 89% cannot be attained even at an acid to toluene molar ratio as high as 18:1. Likewise, using a molar ratio, acid to toluene of say 12:1, the requisite effective product acid concentration would be unattainable even at a reactant acid concentration as high as 94%. Thus both the concentration of the acid reactant and the molar ratio of the acid to toluene must be sufficiently high in order to achieve the required effective product acid concentration of 89% or higher.

Moreover, the attainment of the objectives of the invention is predicated on a combination of (a) operating at the specified effective product acid concentration while (b) using a molar ratio of nitric acid reactant to toluene, in excess of 14:1. In other words, it is not sufficient to operate at the required effective product acid concentration if this is attained by using for example 100% nitric acid reactant and a molar ratio, acid to toluene, of say 8:1. In accordance with the invention a ratio in excess of 14:1, such as about 15:1 to about 25:1, is required to achieve the safety objectives set forth herein. The preferred acid to toluene molar ratio range is from about 16:1 to about 22:1; and for practical and economic considerations it is particularly preferred to use a molar ratio ranging from about 17:1 to about 20:1.

The reactant nitric acid concentration must, of course, be such as to achieve the parameters specified above. Generally, such concentration is in excess of 90%, such as about 93-100%, preferably about 94-100%.

As indicated above, substantial reduction of phenolic by-product formation, i.e., mainly by-product cresol, is achieved by using such nitric acid reactant concentration and molar excess as to attain the specified effective product acid concentration.

The technique for measuring cresol by-product content of DNT is based on ultraviolet (U.V.) light absorbance. The by-products are extracted from the DNT sample with dilute sodium hydroxide washes. The absorbance of the extract is measured at 430 nm and compared to standards prepared using dinitro-ortho-cresol. Synthesis by-products are actually a mixture of cresols and phenolic compounds, but are all referenced against dinitro-ortho-cresol. Although different species will yield varying absorbences, this industry standard method gives a quantitative amount of the overall by-product content and quality of the measured sample. Typical industry standards for DNT require the cresol content measured with the U.V. absorbance method to be less than 350 ppm. DNT, made in a mixed acid system, typically has more than 1,000 ppm cresol content before washing.

The nitration reaction is effected at any suitable temperature such as from about 0° to about 70° C. Generally speaking, too high a reaction temperature may detrimentally affect the isomer distribution of the resulting dinitrotoluene, and this may be important when the resulting DNT is to be used, for example, as an intermediate for making toluene diamine and subsequently toluene diisocyanate. On the other hand, if one were to carry out the reaction at very low temperatures, this would require the use of costly chilling equipment or operations. Thus in accordance with the preferred embodiments, the nitration reaction is effected at a temperature ranging from about 35° to about 60° C. and still more preferably about 40°-54° C.

The process of the invention can be operated batchwise or on a continuous basis, the continuous process being preferred. Typically in a continuous process, the nitric acid and toluene are continuously fed to a single reactor or a series of reactors. Since the nitration reaction is exothermic, cooling means is provided to remove some of the heat of reaction and thereby maintain the reaction mixture at or within the desired temperature. The nitration reaction proceeds step-wise beginning with the conversion of toluene to mononitrotoluene, the latter being further nitrated to dinitrotoluene. The residence time inside the reactor is determined as a function of the temperature. For example, at a temperature of about 50° C. a residence time of approximately 25 minutes is sufficient to bring about the conversion of all the toluene and substantially all the mononitrotoluene to DNT.

The DNT product can then be separated by any suitable means, such as phase separation and, thereafter, purified using conventional methods to achieve the desired degree of purity.

The following examples are provided to illustrate the invention. In these examples, all parts and percentages are by weight unless otherwise specified.

product acid concentration in Comparisons A and B is 87.9% and 88.1%, respectively (i.e., below the 89% minimum specified according to the invention), with a consequent substantial increase in cresol content.

TABLE I

| Example No. | $HNO_3$ Conc. (%) | Molar Ratio $HNO_3$:DNT | Effluent Make-Up DNT | Effluent Make-Up $HNO_3$ | Effluent Make-Up $H_2O$ | Effective Product Acid Concentration | Cresol Content (ppm) in DNT Product |
|---|---|---|---|---|---|---|---|
| 1 | 98 | 18:1 | 14.6% | 80.7% | 4.7% | 94.5% | 182 |
| 2 | 98 | 18:1 | 14.6 | 80.7 | 4.7 | 94.5 | 162 |
| 3 | 93 | 18:1 | 13.9 | 76.9 | 9.3 | 89.3 | 436 |
| Comp. A | 95 | 10:1 | 24.1 | 66.7 | 9.2 | 87.9 | 846 |
| Comp. B | 93 | 14:1 | 17.5 | 72.7 | 9.8 | 88.1 | 747 |

EXAMPLE 1

A jacketed glass reactor was used which was equipped with a stirrer and maintained at a temperature of 40° C. Nitric acid having a concentration of 98% by weight and toluene were fed continuously to the reactor with continuous removal of reaction product mixture after a residence time of 30 minutes. The toluene feed rate was 1.45 grams per minute. The feed rate of the nitric acid was 17.80 grams per minute thus providing a molar ratio nitric acid to toluene of 18:1. Product dinitrotoluene was recovered from the reactor effluent by phase separation, water washed, and analyzed by U.V. absorption for cresol content. The latter was 182 ppm by weight.

On the basis of the make-up of the effluent, the effective product acid concentration was calculated, and the results, including reactor effluent make-up, are summarized in Table I below.

EXAMPLE 2

The identical Procedure of Example 1 was repeated, and the results are shown in Table I.

EXAMPLE 3

Again, the identical procedure of Example 1 was followed except that the nitric acid feed had a concentration of 93% instead of 98%. The results are provided in Table I.

COMPARATIVE DETONATION TESTING

The ability of various nitric acid/dinitrotoluene mixtures to detonate was tested using 325 mls. (corresponding to about 450 grams) of each mixture. In each test, the mixture was placed in a cylindrical steel container 200 mm high with an outside diameter of 60 mm and an inside diameter of 50 mm. The container rested on a steel disk (dia. 40 mm, height 4.5 mm) which in turn rested on a cylindrical solid lead block 70 mm high by 40 mm diameter. The lead block was supported by another steel disk of the same dimension as the disc resting on top of the block. The cylindrical container was closed with a polypropylene lid having a hole through which a thin glass test tube was inserted containing 3 grams of a primer, namely, pentaerythritol tetranitrate (PETN). A remotely controlled electromagnetic exploder was used to ignite the PETN.

In the case of each mixture, after each shot, the condition of the lead block and the cylindrical container were examined to make a semiquantitative assessment of the detonatability of each mixture.

Four mixtures were subjected to this detonation test as well as a control run wherein the test was run with 100% nitric acid, i.e., no DNT and no water. The mixtures make-up and the detonative test result are reported in Table II below.

The data in Table II demonstrates the criticality of the selective molar ratio range, acid to toluene, which is specified herein to reducing the risk or hazard of explosion associated with the toluene nitration reaction.

TABLE II

| Test No. | Mixture Make-Up % $HNO_3$ | Mixture Make-Up % DNT | Mixture Make-Up % $H_2O$ | Molar Ratio $HNO_3$:DNT | Corresp. Molar Ratio $HNO_3$:Toluene in Reactor Feed Using 98% $HNO_3$ | Observed Results |
|---|---|---|---|---|---|---|
| 1 | 100 | 0 | 0 | Blank | Blank | Container bulged |
| 2 | 65 | 28 | 7 | 6.7:1 | 9:1 | Container pulverized |
| 3 | 70 | 24 | 6 | 8.4:1 | 11.1 | Container pulverized |
| 4 | 78 | 17 | 5 | 13.3:1 | 15:1 | Container split in many pieces |
| 5 | 81 | 14 | 5 | 16.7:1 | 18:1 | Container bulged |

COMPARISONS A AND B

For purposes of comparison, the identical procedure of Example 1 was followed with the following modifications: In Comparison A, 95% nitric acid was used at a feed rate to provide a molar ratio, nitric acid to toluene, of 10:1; and in Comparison B, 93% nitric acid was used as a feed rate to provide a molar ratio, nitric acid to toluene of 14:1. The results of these two comparisons are summarized in Table I. As indicated, the effective While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. An improved process for preparing dinitrotoluene which comprises reacting in the liquid phase toluene with nitric acid having a concentration in excess of 90%, the reaction being carried out using such relative proportions of reactants as to provide (a) a molar ratio of nitric acid to toluene in excess of 14:1 and (b) an effective product acid concentration of at least 89%.

2. The process of claim 1 wherein said molar ratio of nitric acid to toluene is from about 15:1 to about 25:1.

3. The process of claim 1 wherein said effective product acid concentration is from about 90% to about 96%.

4. The process of claim 1 wherein said reaction is carried out at a temperature of from about 0° C. to about 70° C.

5. The process of claim 4 wherein said temperature is from about 35° C. to about 60° C.

6. The process of claim 2 wherein said effective product acid concentration is from about 90% to about 96%.

7. The process of claim 6 wherein said temperature is from about 35° C. to about 60° C.

8. The process of claim 7 wherein said molar ratio is from about 16:1 to about 22:1.

9. The process of claim 7 wherein said molar ratio is from about 17:1 to about 20:1.

10. The process of claim 9 wherein said temperature is from about 35° C. to about 60° C.

11. In a process for producing dinitrotoluene by the liquid phase reaction of toluene with nitric acid, the improvement of employing such relative proportions of reactants as to provide (a) a molar ratio of nitric acid to toluene in excess of 14:1 and (b) an effective product acid concentration of at least 89%.

12. The process of claim 11 wherein the dinitrotoluene product contains less than about 350 ppm of cresol.

13. The process of claim 11 wherein said reaction is carried out at a temperature from about 35° C. to about 60° C.

14. The process of claim 13 wherein said molar ratio is from about 15:1 to about 25:1 and said effective product acid concentration is from about 90% to about 96%.

15. The process of claim 12 wherein said molar ratio is from about 16:1 to about 22:1 and said reaction is carried out at a temperature from about 35° C. to about 60° C.

16. The process of claim 15 wherein said molar ratio is from about 17:1 to about 20:1.

17. The process of claim 16 wherein said reaction temperature is from about 40° C. to about 54° C.

* * * * *